United States Patent [19]
Winkler

[11] Patent Number: 6,161,734
[45] Date of Patent: Dec. 19, 2000

[54] APPARATUS FOR DISPENSING VISCOUS COMPOUNDS

[75] Inventor: Siegbert Winkler, Feldkirch, Austria

[73] Assignee: Ivoclar AG, Schaan, Liechtenstein

[21] Appl. No.: 09/351,211

[22] Filed: Jul. 12, 1999

Related U.S. Application Data
[60] Provisional application No. 60/101,217, Sep. 21, 1998.

[30] Foreign Application Priority Data

Jul. 23, 1998 [DE] Germany .............................. 198 33 238

[51] Int. Cl.$^7$ ................................................. G01F 11/00
[52] U.S. Cl. ............................................................. 222/390
[58] Field of Search ..................................... 222/390, 326, 222/327

[56] References Cited

U.S. PATENT DOCUMENTS 2,745,575  5/1956  Spencer ................................... 222/327
2,874,877  2/1959  Spencer ................................. 222/390 X
4,457,641  7/1984  Smith ..................................... 222/390 X
5,076,473  12/1991 Steiner .................................. 222/390 X

FOREIGN PATENT DOCUMENTS 27 41 185  2/1979  Germany .

Primary Examiner—Kevin Shaver
Assistant Examiner—Thach H Bui
Attorney, Agent, or Firm—John C. Thompson; Alan S. Korman

[57] ABSTRACT

An apparatus for dispensing a viscous compound has a dispensing device and a sleeve having a first end detachably connected to the dispensing device. The dispensing device has a plunger and a rotary drive acting on the plunger for applying pressure onto the viscous compound contained in a container attached to the dispensing device for dispensing the viscous compound. The dispensing device has an actuator that couples the rotary drive to the plunger. When the sleeve is attached to the dispensing device, the actuator allows movement of the plunger in the dispensing direction of the dispensing device upon actuation of the rotary drive.

14 Claims, 3 Drawing Sheets

APPARATUS FOR DISPENSING VISCOUS COMPOUNDS

This application claims benefit of Provisional Application 60/101,217 filed Sep. 21, 1998.

BACKGROUND OF THE INVENTION

The present invention relates to an apparatus for dispensing viscous compounds, especially dental materials.

The apparatus comprises a dispensing device to which a sleeve is detachably attached whereby the dispensing device has a rotary drive with which via a plunger pressure is applied to the compound received in a container for dispensing the compound through the sleeve.

Such an apparatus is known from German Patent 27 41 185. In this device a rotary drive is provided which is embodied as a nut that is rotatably supported on a housing.

The threaded rod has a trapezoidal thread with great pitch, and a preadjustment of the apparatus is possible by a manipulator acting on the threaded rod.

The apparatus is used such that the manipulator at the end of the threaded rod is held between thumb and index finger and the nut is then turned by the thumb. This allows for a fine adjustment.

The dispensing or pressing out of viscous compounds from sleeves, which may be part of a capsule or cartridge, requires, depending on the respective situation, greatly different actuation forces. When rather liquid, but still viscous compounds must be dispensed from sleeves with a small diameter, the actuating forces are minimal. However, when relatively viscous materials must be pressed out of cartridges with large diameter, especially when through a narrow tip, rather great actuating forces are required. The aforementioned patent suggests an alternative embodiment of the apparatus made of metal. However, this apparatus, because of its size and because of the relatively great pitch, is suitable substantially only for compounds in thin sleeves.

In order to accommodate various types of applications, it has been customary to employ complete syringes as disposable articles. They comprise a rotary drive which is adjusted in its size to the compound to be dispensed. This allows for a relatively precise adaptation according to the specific requirements. However, it is disadvantageous that considerable amounts of plastic waste are produced which possibly is even greater than the amount of the dental material to be dispensed.

In numerous other designs, pistol-shaped apparatus are known in which a sleeve filled with dental material is used and the actuation of the pistol grip causes dispensing of the dental material from the sleeve. It is possible to realize dispensing forces that surpass up to five times the manually applied force by employing respective gear ratios in order to be able to dispense compounds of high viscosity.

On the other hand, a rotary drive is easier to fine adjust and is basically also suitable for transmitting large actuating forces.

It is therefore an object of the present invention to provide an apparatus of the aforementioned kind which is suitable for dispensing compounds from sleeves having a relatively large diameter whereby the compounds are highly viscous and whereby a fast adaption to the filling degree of the sleeve is possible. Furthermore, no separate disposable dispensing device for each sleeve should be required.

SUMMARY OF THE INVENTION

The apparatus according to the present invention comprises a dispensing device having an actuator which, upon insertion of the sleeve into the dispensing device, realizes a threaded engagement with the rotary drive and which actuates the advancement of the plunger upon turning of the rotary drive.

It is especially advantageous that despite the use of a threaded rod that, in principal, is suitable for great actuating forces, a quick adaptation to the degree of filling of the respectively employed sleeve is possible. Inventively, the threaded rod of the rotary drive can be freely moved by the rotary drive wheel when the sleeve is not attached. The rotary drive wheel is guided in slots at the rear part of the dispensing device. This inventive feature allows to preadjust the threaded rod and to select a position in which the forward end or the spindle abutment are not yet in abutment at the piston of the sleeve. The sleeve is then inserted into the dispensing device and locked therein. Only upon locking of the sleeve is the threaded position activated so that the threaded rod can no longer be axially moved but can only be rotated. In this state a very fine adjustment and reliable actuation and dispensing of the dental compound are possible.

It is especially advantageous that this inventive solution can be realized without complicated measures. Inventively, the actuator is preferably embodied as a pressure member and is activated by the rearward end of the sleeve and acts on the threaded jaws. The threaded jaws slide along slanted surfaces radially inwardly so that in their closest position they act as a nut that is fixedly connected to the housing of the dispensing device. The length of the threaded jaws is preferably slightly greater than the diameter of the threaded rod so that a uniform force introduction and a minimal surface pressure are realized.

Despite the great flexibility of the inventive apparatus the use of a simple sleeve as the only disposable part is possible. The sleeve preferably has a small piston which is pressure loaded by the spindle abutment.

If necessary, it is also possible to adapt the apparatus to sleeves of a smaller diameter, for example, by employing a ring insert inserted into the receiving part for the sleeve provided at the dispensing device. The sleeve of smaller diameter is then inserted into the ring insert.

The sleeve has a first end facing the dispensing device. This first end provides an abutment surface for the inventive pressure member. The pressure member surrounds the plunger or spindle abutment circular-symmetrically so that a uniform pressure distribution is provided. It transmits the pressure forces of the sleeve, inserted and locked by rotation, onto the threaded jaws which are guided along slanted surfaces and, upon respective pressure loading by the pressure member, are radially inwardly moved. In order to ensure symmetric gliding, two axially spaced slanted surfaces can be provided along which the respective counter surfaces of the threaded jaws glide.

Preferably, the gliding angle of the threaded jaws is approximately 45° so that the slanted surfaces of the threaded jaws as well as the inner surfaces of the dispensing device facing the slanted surfaces of the threaded jaws extend at this angle.

Preferably, the threaded jaws are spring loaded in the radially outwardly direction so that they automatically release the threaded rod when no sleeve is received in the dispensing device.

In a preferred embodiment, the rotary drive has a rotary drive wheel that is recessed as will be explained in the following. The apparatus is preferably of a two part construction and has a front part and a rear part which are connected to one another by a rotary joint. The rotary drive wheel extends in slots of the rear part and is fixedly connected thereto so that upon relative rotation of the front part to the rear part the rotary drive wheel and thus the threaded rod are rotated in the threaded jaws and produce advancement of the plunger.

It is especially advantageous in this context that the rear part is held stationary and the front part is rotated relative to it.

In an alternative embodiment, the rear part is secured at the front part. A rotation of the rotary drive wheel is then possible by engaging the drive wheel through the slots. In both cases a steady support at the rear part of the dispensing device is possible.

The two embodiments, when adjusted properly to the length of the sleeve, allow for easy detection of the remaining amount of dental material. When the rotary drive wheel has reached the forward end of the slot, the dental material is almost completely dispensed.

The force transmission between the actuating device, i.e., the threaded rod and the threaded jaws, depends also on the type of thread employed. Preferably, a circular embodiment of the thread is used which has the advantage that comparatively minimal radially outwardly acting forces are generated during force transmissions so that the two threaded jaws are not subjected to greatly diverging forces.

It is understood that instead of the disclosed embodiment of the actuating drive any other drive can be used which upon insertion of the sleeve will bring the threaded jaws into engagement at the threaded drive member. For example, in an alternative embodiment it is suggested to move, by a pin or a sleeve, a ring member that has at its inner surface an inner cone. The inner cone works together with correspondingly shaped abutment surfaces of threaded jaws which are moved upon movement of the inner cone in the radially inward direction.

Furthermore, the slant of the inventive slanted surfaces can be varied in a wide range according to the needed specifications. Preferably, the slant of the slanted surfaces is selected such that upon actuation of the actuator the threaded jaws are moved from the second into the first position by a travel stroke which corresponds to slightly more than the depth of the thread. This provides for a certain safety reserve which prevents that the threaded jaws will not completely release the thread when the second position is to be reached.

The spring force acting on the threaded jaws is preferably designed such that at least a part of the force component acts radially outwardly. When the sleeve is removed from the dispensing device, it is thus ensured that the threaded jaws are moved safely into the second position. According to a preferred embodiment, it is suggested that the spring force of the springs employed act parallel to the slanted surfaces.

Furthermore, it is especially advantageous to provide the sleeve at its first end with collar-type radial projections and at its end face with an abutment surface for the pressure member. Preferably, the thickness of the material of the projections is slightly greater than the wall thickness of the sleeve so that a safe anchoring at the corresponding abutment shoulders of the dispensing device is ensured even for great dispensing forces.

In this context it is also favorable when the collar projections are relatively wide so that they are able to receive great loads. The sum of the angles covered by them can be slightly less than approximately 180°. By simple rotation of slightly less than 45°, when four collar projections and four axially acting shoulders are used, a safe anchoring of the sleeve at the dispensing device is ensured, The rotation can simply be limited in the manner of a bayonet closure by a rotary stop which can be provided in the form of a pin.

BRIEF DESCRIPTION OF THE DRAWINGS

The object and advantages of the present invention will appear more clearly from the following specification in conjunction with the accompanying drawings, in which.

DESCRIPTION TO PREFERRED EMBODIMENTS

Figure 1:
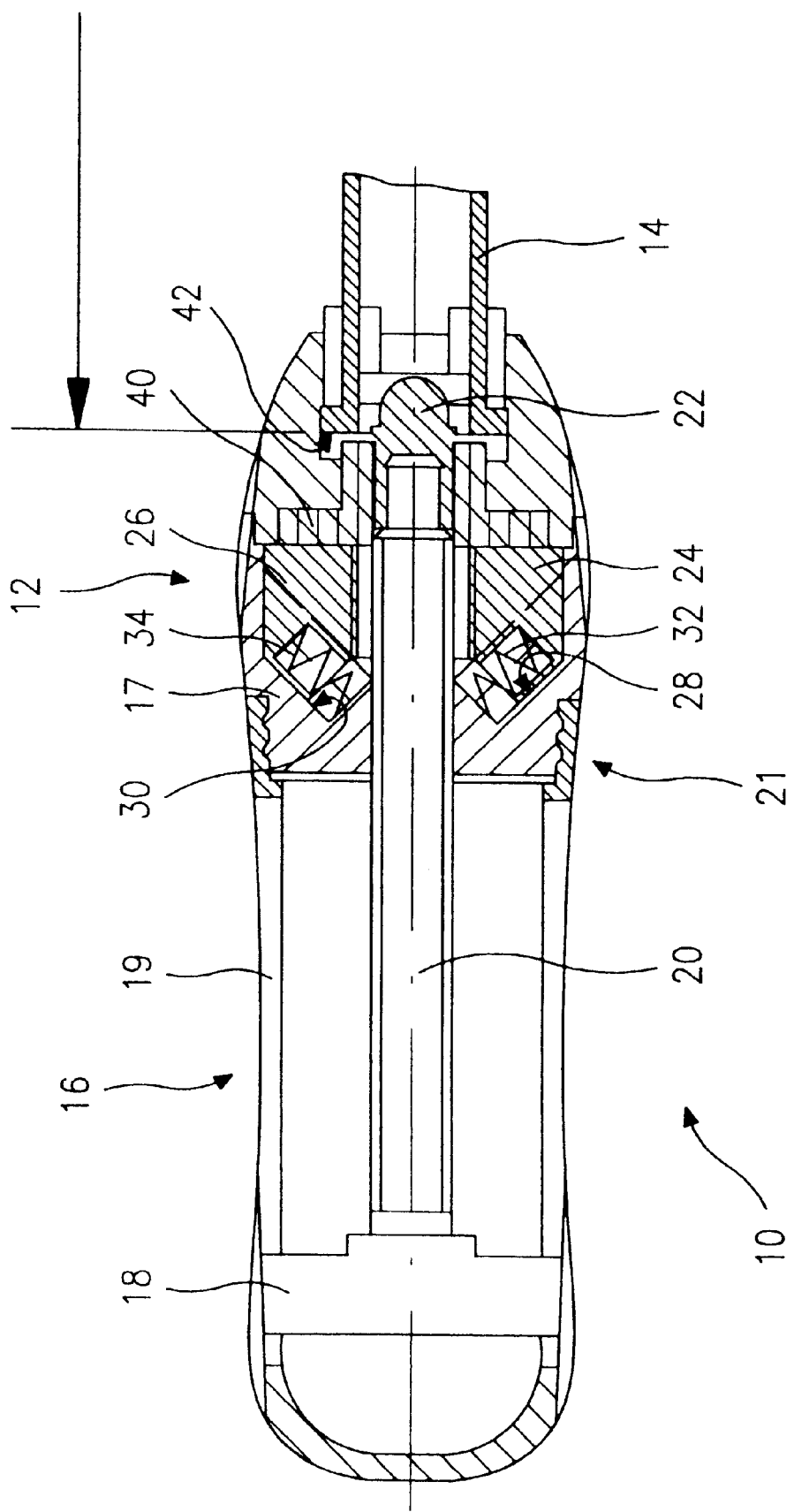
FIG. 1 shows a sectional view of the inventive apparatus and also the position of the sleeve connected thereto.

The present invention will now be described in detail with the aid of several specific embodiments utilizing FIGS. 1 through 3.

An apparatus 10 according to FIG.. 1 comprises a dispensing device 12 into which a sleeve 14 is inserted. Even though the shown embodiment shows a simple sleeve, it is understood that the sleeve may be part of a capsule or a cartridge and that direct dispensing of the dental material contained therein via a dispensing tip is possible.

The apparatus 10 comprises further a rotary drive 16 which comprises a rotary drive wheel 18 and a threaded rod 20. The dispensing device 12 in the shown embodiment is of a two part construction and has a front part 17 that is rotatably supported at the rear part 19. The rotary drive wheel 18 is fixedly but axially slidably connected within the rear part 19. The rear and the front parts are connected to one another by a rotary joint 21 that provides a safe axial support but easy rotation.

In a modified embodiment it is possible to secure the front and rear parts 17, 19 fixedly at one another and to allow access of the rotary drive wheel for rotation of the rotary drive through slots 52 and 54. In this embodiment the rotary drive wheel 18 is a disk with projections which project Into the slots 52, 54 and are entrained therein.

The first position represented in FIG. 1 illustrates that there is no engagement of the dispensing device 12 at the threaded rod 20. Accordingly, the threaded rod 20 as the actuating rod is axially freely moveable. At its front end it is supported rotatably in a plunger or a spindle abutment 22 having a rounded tip that is designed to load the non-represented piston in the sleeve 14 with dispensing forces.

In order to provide for a threaded engagement, two oppositely arranged threaded jaws 24 and 26 are provided which are moveable radially as well as axially. The dispensing device 12 has inwardly and forwardly slanted surfaces 28 and 30 which abut matching counter surfaces of the threaded jaws 24 and 26. Pressure springs 32 and 34 which are received partly in the threaded jaws 24 and 26 force the threaded jaws 24 and 26 along the slanted surfaces forwardly and outwardly so that no threaded engagement is realized.

The threaded jaws 24, 26 are semicircular and have an inner thread that extends substantially about 180°. In the position represented in FIG. 2 they act as a nut.

For actuating the threaded jaws, an actuator 40 is provided which extends as a pressure member between the threaded jaws 24, 26 and an abutment surface 42 of the sleeve 14. The pressure member is axially moveably supported but serves at the same time as a support of the forward end of the threaded rod which is supported at the spindle abutment 22 within the dispensing device 12.

Figure 2:
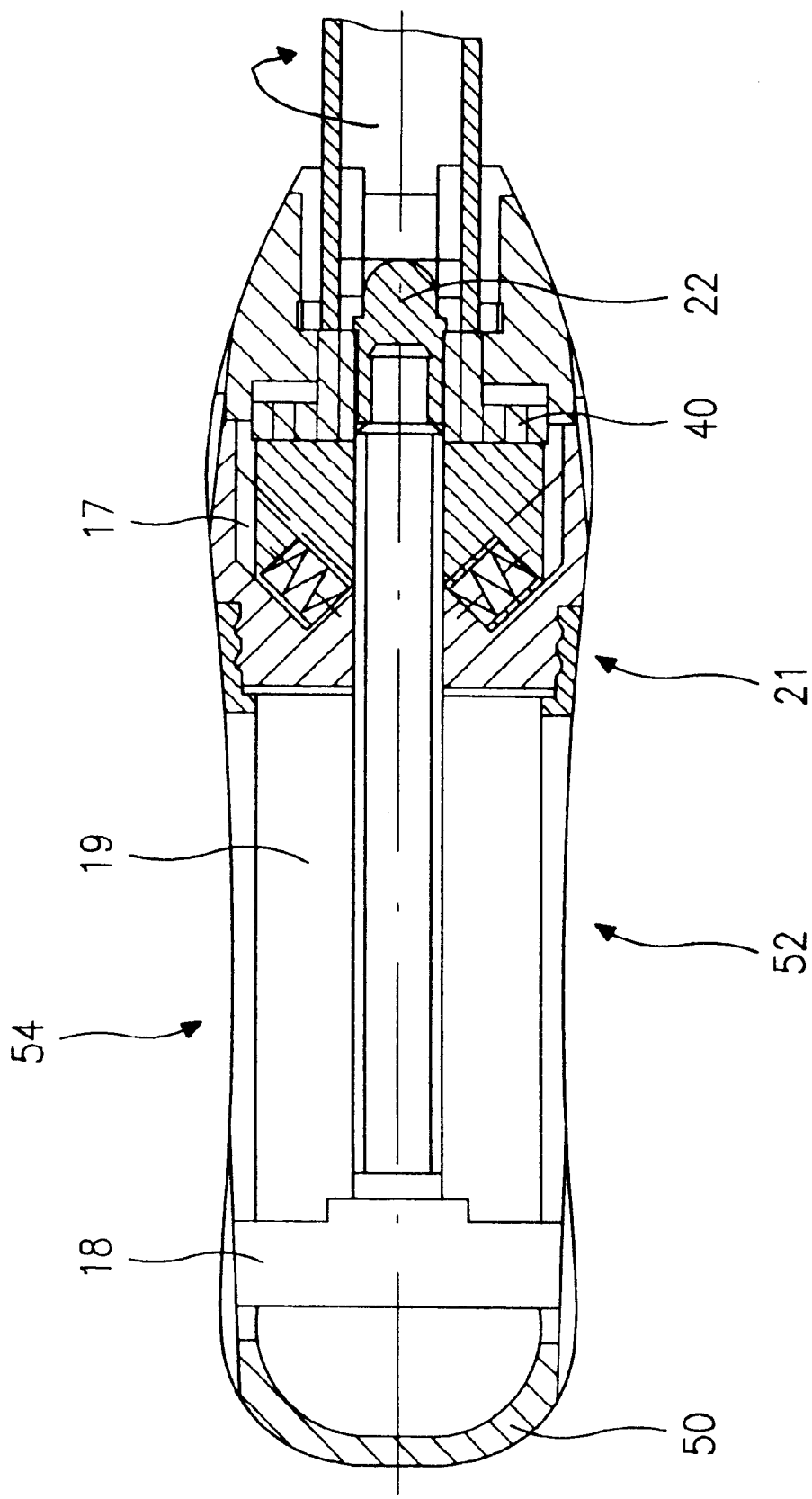
FIG. 2 shows a further sectional view of the apparatus in the embodiment according to FIG. 1 with the sleeve anchored at the dispensing device and also shows the position of the sleeve relative to the dispensing device.
Figure 4:
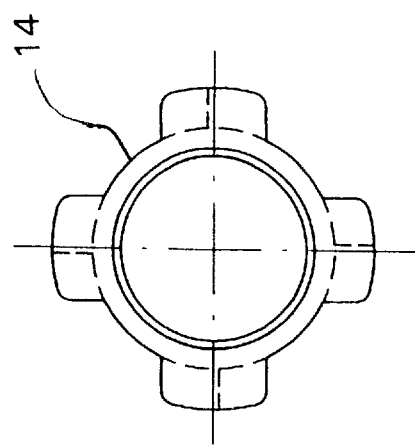
FIGS. 4 and 5 are end and side views, respectively, of the sleeve shown in FIG. 3.
Figure 5:
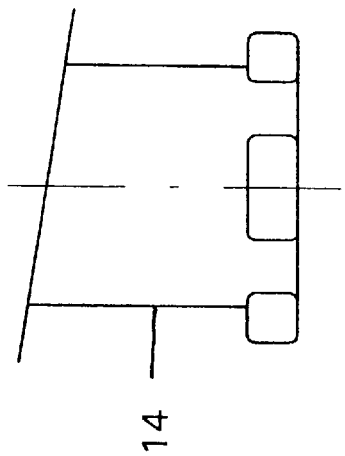

The sleeve 14 ends at its first end facing the dispensing device 12 in collar-type radial projections 44 whereby the embodiment according to FIGS. 1 and 2 four such collar projections are provided which are uniformly distributed in the circumferential direction of the sleeve 14. The radial collar projections 44 form together with matching axially acting abutment shoulders of the dispensing device 12 a type of bayonet closures so that a safe anchoring of the sleeve 14 in the dispensing device 12 is possible when the sleeve is in the position shown in FIG. 2.

When comparing FIGS. 1 and 2, it is apparent that the sleeve in the position shown in FIG. 2 penetrates deeper into the corresponding receiving opening of the dispensing device 12. Furthermore, the sleeve 14, as can be seen in the representation to the right in FIG. 2, is rotated by slightly less than 45° so that the radial collar projections 44 engage behind the abutment shoulders and thus can not be dislodged from the dispensing device even when great pressure forces are applied. Its abutment surface 42, that includes also the collar projections 44, actuates the actuator 40 which is thus displaced in the axial direction to the rear.

The actuator 40 thus axially exerts pressure onto the threaded jaws 26 which are thus moved along the coordinated slanted surfaces 28 and 30 against the spring force of the springs 32 and 34 in the radial inward and axially rearward direction. The movement in the axial direction proceeds until the threaded jaws 24 and 26 are in maximum threaded engagement, while the collar projections 44 resting at the abutment shoulders. In this position, the pressure springs 32 and 34 are compressed to the maximum extent whereby the required insertion force for the sleeve into the dispensing device 12 is adjustable.

The second position represented in FIG. 2 allows applying the required dispensing force onto the piston of the sleeve 40 by rotating the rotary drive wheel 18 and thus moving the spindle abutment 22.

The embodiment represented in FIGS. 1 and 2 relates to dispensing of dental material from a sleeve that is completely filled. In practice, it is desirable when the same dispensing device 12 can be used to dispense material from different sleeves 14 containing different materials. For this purpose, the sleeve 14 must be exchanged which is inventively easily possible when the sleeve 14 is rotated in the direction indicated by the arrow in the right half of FIG. 2 so that the sleeve can be removed from the dispensing device 12.

In order to be able to further empty a partly empty sleeve, the rotary drive wheel 18 must be moved first axially forwardly until the spindle abutment rests at the piston. Since the threaded rod without threaded engagement at the jaws can be easily axially displaced, this position can be easily reached. Preferably, the threaded rod is then returned by a short distance, for example, approximately 2 to 3 nm. This ensures that the insertion of the sleeve 14 into the dispensing device 12 does not result in dispensing of dental material. In this position, the spindle abutment 22 is then located in direct vicinity of the sleeve and the rotary drive wheel 18 is located approximately at half the possible actuating path. Insertion of the sleeve 14 then results in threaded engagement of the threaded jaws 24, 26 so that dispensing can begin.

Preferably, the rear part 19 has a rounded portion 50 so that the dispensing device 12 at its rear end is of a somewhat spherical design that is user-friendly. This allows excellent guiding by hand when axial pressure must be applied during dispensing.

Figure 3:
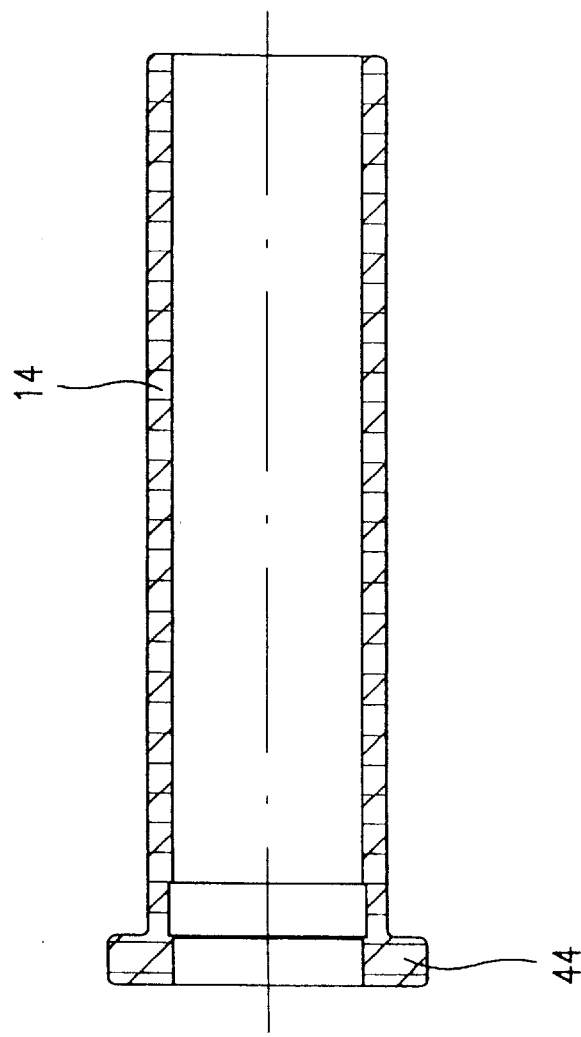
FIG. 3 shows a sectional view of the sleeve for use in the inventive dispensing device.

FIG. 3 shows a sleeve 14 In section. The axial length of the sleeve 14 is somewhat smaller than the axially length of the slots 52 and 54 so that with the inventive dispensing device 12 a complete emptying of the dental material contained within the sleeve 14 is possible.

As can be seen in FIG. 3, the thickness of the radial collar projections 44 is slightly greater, for example, twice as great as the thickness of the sleeve so that a safe anchoring is possible.

It is understood that instead of the sleeve 14 a complete cartridge can be inserted which has a dispensing end into which a correspondingly shaped piston can penetrate in order to empty the dental material completely from the cartridge.

What is claimed is:

1. An apparatus (12) for dispensing a compound from a sleeve (14), one end of the sleeve capable of being pushing into the apparatus for assembly thereto; the apparatus comprising:

a housing (17, 19);

a rotary drive (16) mounted within the housing, the rotary drive including a threaded rod (20) and a plunger (22) at one end of the threaded rod, which plunger can engage a piston within the sleeve (14);

threaded jaws (24, 26) carried by the housing and movable radially into and out of engagement with the threaded rod; and an actuator (40) carried by the housing for forcing the threaded jaws into engagement with the threaded rod when the sleeve is pushed into the apparatus, and which will permit the threaded jaws to move away from the threaded rod when the sleeve is removed from the apparatus to permit free axial movement of the threaded rod.

2. An apparatus according to claim 1, wherein said sleeve (14) has a rearward end forming an abutment surface (42) and wherein said actuator (40) abuts said abutment surface (42).

3. An apparatus according to claim 2, wherein at least two of said threaded jaws (24, 26) are positioned opposite one another on opposite sides of said threaded rod (20), wherein said threaded jaws (24, 26) are moveable in a direction perpendicular to an axis of rotation of said rotary drive (16) for engaging and releasing said threaded rod (20).

4. An apparatus according to claim 2, wherein:

said dispensing device (12) has slanted surfaces (28, 30);

said threaded jaws (24,26) have slanted surfaces (28, 30);

said slanted surfaces (28, 30) of said threaded jaws (24, 26) are slidably supported at said slanted surfaces (28, 30) of said dispensing device (12); and said threaded jaws (24, 26) have a first position in which said threaded jaws engage said threaded rod (20) and have a second position In which said threaded jaws (24, 26) release said threaded rod (20).

5. An apparatus according to claim 4, wherein said threaded jaws (24, 26) in said second position are spring loaded against said dispensing device (12).

6. An apparatus according to claim 5, wherein said sleeve (14) has outwardly extending radial projections (44) for anchoring said sleeve (14) at said dispensing device (12).

7. An apparatus according to claim 6, wherein said dispensing device (12) has engagement elements and wherein said radial projections (44) engage said engagement elements.

8. An apparatus according to claim 7, wherein:

a plurality of said radial projections (44) are uniformly circumferentially distributed about said first end of said sleeve (14);

said engagement elements are shoulders;

said radial projections (44) engage said shoulders when said sleeve (14) is inserted into said dispensing device (12) and rotated by a locking angle into a locking position;

said shoulders axially secure said radial projections (44) in said locking position.

9. An apparatus according to claim 8, wherein four of said radial projections are provided.

10. An apparatus according to claim 7, wherein said actuator (40) has a pressure member and wherein said sleeve (14) is inserted into said dispensing device (12) against a force exerted by said pressure member and are spring-loaded.

11. An apparatus according to claim 1, wherein said rotary drive (16) comprises a spindle abutment (22) fixedly connected to said threaded rod (20).

12. An apparatus according to claim 2, wherein said threaded jaws (24, 26) each have a slanted surface having a normal pointing radially outwardly in a direction away from said sleeve (14) and wherein said dispensing device (12) has a slanted radially inwardly facing surface abutting said slanted surfaces of said threaded jaws (24, 26), wherein said slanted surfaces of said threaded jaws (24, 26) extend at least over a portion of a length of said threaded yaws (24, 26).

13. An apparatus according to claim 10, comprising a common spring for loading said threaded jaws (24, 26) and said sleeve(14).

14. An apparatus according to claim 1, wherein said dispensing device (12) has a front part (17) and rear part (19) and a rotary joint connecting said front part (17) and said rear part (19).

* * * * *